US012594357B2

(12) United States Patent
Carter et al.

(10) Patent No.: US 12,594,357 B2
(45) Date of Patent: Apr. 7, 2026

(54) TORCHIERE WITH AIR FLOW MECHANISM AND ULTRAVIOLET DISINFECTION

(71) Applicants: Brian D. Carter, Baldwinsville, NY (US); Eric A. Schiff, Dewitt, NY (US)

(72) Inventors: Brian D. Carter, Baldwinsville, NY (US); Eric A. Schiff, Dewitt, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 732 days.

(21) Appl. No.: 17/944,548

(22) Filed: Sep. 14, 2022

(65) Prior Publication Data

US 2023/0079206 A1     Mar. 16, 2023

Related U.S. Application Data

(60) Provisional application No. 63/244,470, filed on Sep. 15, 2021.

(51) Int. Cl.
*A61L 9/20*          (2006.01)
(52) U.S. Cl.
CPC ............. *A61L 9/20* (2013.01); *A61L 2209/11* (2013.01); *A61L 2209/12* (2013.01); *A61L 2209/134* (2013.01); *A61L 2209/15* (2013.01)

(58) Field of Classification Search
None
See application file for complete search history.

(56) References Cited

U.S. PATENT DOCUMENTS

| | | | | |
|---|---|---|---|---|
| 2,350,462 | A * | 6/1944 | Johns ...................... | F21V 33/00 |
| | | | | D26/112 |
| 6,322,614 | B1 * | 11/2001 | Tillmans ................. | F24F 7/065 |
| | | | | 95/287 |
| 6,939,397 | B2 * | 9/2005 | Nelsen ...................... | F24F 8/80 |
| | | | | 422/124 |
| 2023/0190984 | A1 * | 6/2023 | Whitehead ............... | B01J 35/39 |
| | | | | 422/4 |

* cited by examiner

*Primary Examiner* — Jelitza M Perez
(74) *Attorney, Agent, or Firm* — Bond, Schoeneck & King PLLC; David L. Nocilly

(57) ABSTRACT

A torchiere style sanitizing device for disinfecting airborne pathogens while providing aesthetic area lighting. A reversible fan exchanges air between the upper room air plume and the lower air plume by passing the air through a center disinfecting section. The disinfection section may include a linear UV-C light, reflective tube, and light trap positioned at one or both ends of the disinfection section to maximize the exposure of the air to the UV-C light and contain the UV-C light within the device. The device includes a conventional illumination source in an upper shade and can selectively provide one of more of room air flow, room air disinfection, and room illumination.

12 Claims, 3 Drawing Sheets

TORCHIERE WITH AIR FLOW MECHANISM AND ULTRAVIOLET DISINFECTION

CROSS-REFERENCE TO RELATED APPLICATIONS

The present application claims priority to U.S. Provisional Application No. 63/244,470 filed on Sep. 15, 2021.

BACKGROUND OF THE INVENTION

1. Field of the Invention

The present invention relates to free standing lighting devices and, more specifically, a torchiere with the capability to provide air circulation and ultraviolet radiation for disinfection anywhere within a location.

2. Description of the Related Art

The COVID-19 pandemic has intensified the need for adequate and efficient purification and sanitization of the air in enclosed locations against the presence of airborne pathogens. Conventional approaches for doing so may involve disinfection in central HVAC systems that may be unavailable or costly to install and operate. Wall and ceiling mounted air filtration/disinfection devices are available for individual rooms, but may again be costly or may not integrate well with a room's furnishings. While some desktop devices, such as desk lamps with filtration or purification elements have been proposed, these systems disinfect relatively small flows of air. Accordingly, there is a need in the art for a device that can easily and thoroughly disinfect the air in an enclosed location while integrating naturally into the location.

BRIEF SUMMARY OF THE INVENTION

The present invention is a torchiere style sanitizing device having a self-contained, UV-C lamp for disinfecting airborne pathogens and providing aesthetic area lighting. The device exchanges air between the upper room air plume and the lower, through the unit by means of a reversible fan. The center section disinfects the air with a linear UV-C light before it is discharged at the bottom or top. The lamp safely sanitizes the air by containing the UVC radiation within the torchiere with the use of an Archimedes screw light block on the top and optionally the bottom of the disinfection section. The Archimedes screw can be fabricated to act either as a UV-C absorber or a UV-C backreflector and also can potentially reduce fan noise leaving the device. The disinfection section may be coated on the interior with UV-C reflective material to maximize the internal UV-C intensity. The base may be lined with an acoustic dampening foam to reduce fan noise. The torchiere provides area lighting by means of an LED ring at the top. The device may be operated in lighting, air movement, and disinfecting mode or any combination. The device is portable and requires no installation.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
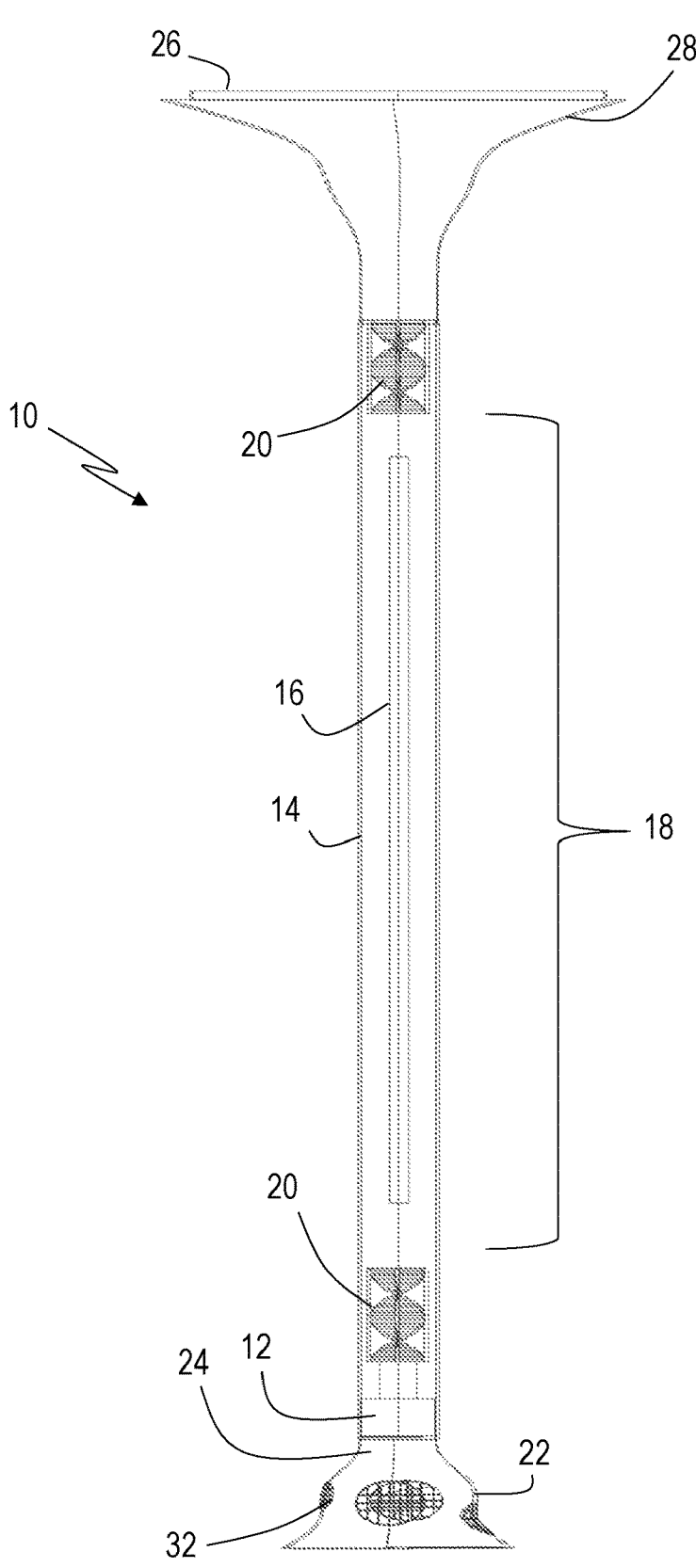
FIG. 1 is a schematic of a portable, vertical air flow ultraviolet (UV) air purification device according to the present invention.

Referring to the figures, wherein like numbers refer to like parts throughout, there is seen in FIG. 1 a torchiere 10 that comprises a self-contained, UV-C lamp for disinfecting airborne pathogens while providing aesthetic area lighting. Torchiere 10 includes a reversible fan 12 that can exchange air between the upper room air plume and the lower. Fan 12 can be driven to move air through a tubular center column 14 that includes a linear UV-C light source 16 to form a disinfection chamber 18 that disinfects the air before it is discharged at the bottom or top, depending on the direction of the reversible fan 12 is driven. Reversible flow allows for the exchange of air from the upper room air zone and the lower floor zone, thereby providing displacement ventilation that provides the benefits of a room ceiling fan as well as energy savings. UV-C light source 16 safely sanitizes the air, and the UV-C radiation is safely contained within disinfection chamber 18 by tubular center column 14 of torchiere 10.

Figure 2:
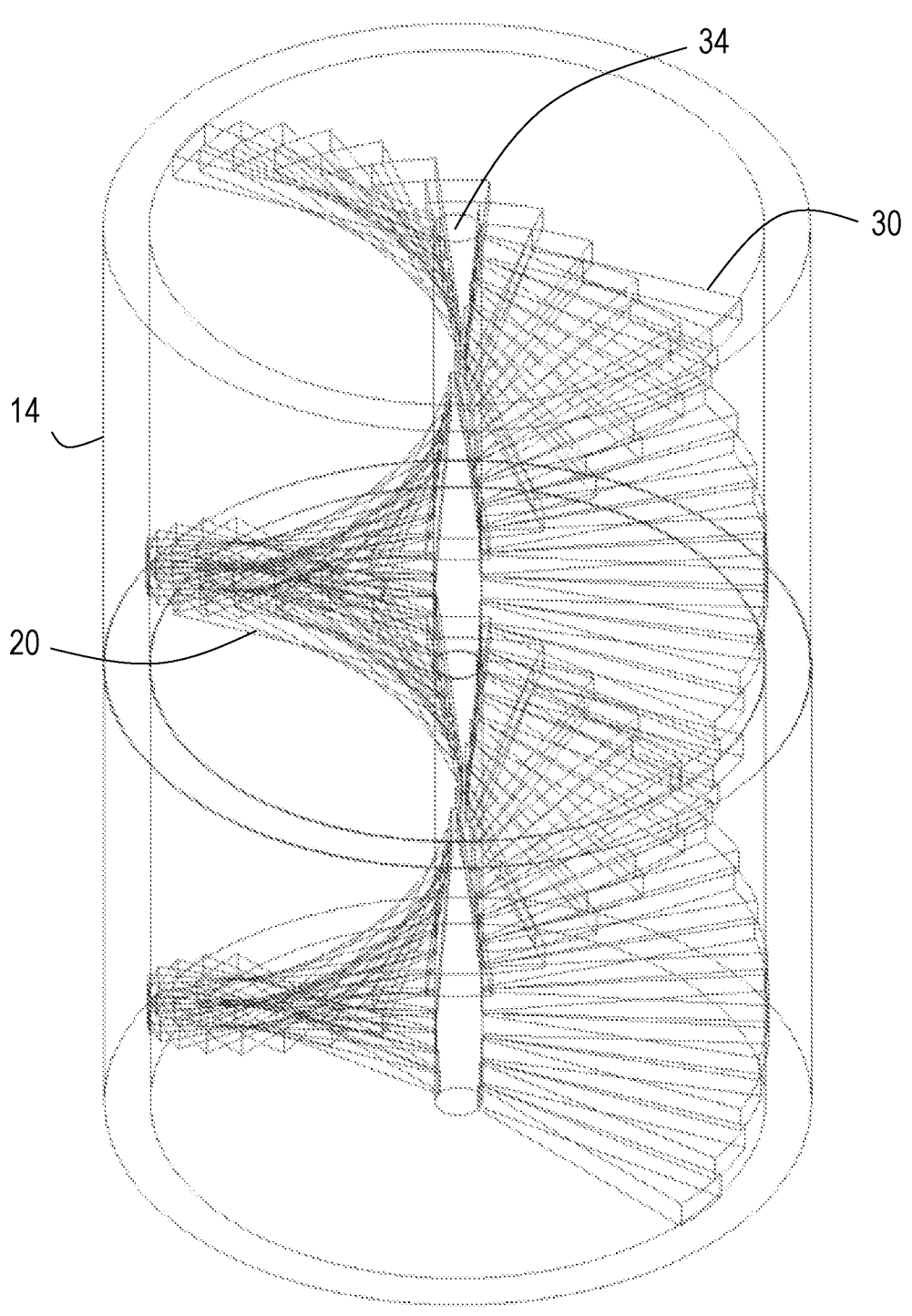
FIG. 2 is a schematic of a two-blade Archimedes screw light-block according to the present invention.

Disinfection chamber 18 comprises two Archimedes screw light-blocks 20 positioned in tubular column 14 of torchiere 10. One light-block is illustrated in more detail in FIG. 2, which shows the implementation of an Archimedes screw with two opposing blades 30 blades extending outward from a central column 34 and, optionally, two complete revolutions for each blade 30. The light-block may consist of UV-C absorbing material. Alternately, the light-block may have a UV-C reflecting surface that is stepped so that the light-block acts as a UV-C back-reflector that reflects light inward to disinfection chamber 18. Disinfection chamber 18 may be coated on its interior surface with UV-C reflective material.

Torchiere 10 includes include a base 22 that houses fan 12 and may be lined with an acoustic dampening foam to reduce fan noise and may include a dust filter 24 for further air purification. Base includes one or more vents 32 in communication with tubular center column 14 and may be elevated above the floor on a stand. Torchiere 10 provides visible illumination using an LED ring 26 positioned above the upper shade 28 of torchiere 10. Torchiere 10 may be operated in a lighting only mode, an air movement only mode, and a disinfecting mode, or any combination thereof. As described above, torchiere 10 is highly portable and does not require any specialized installation or training for use.

Figure 3:
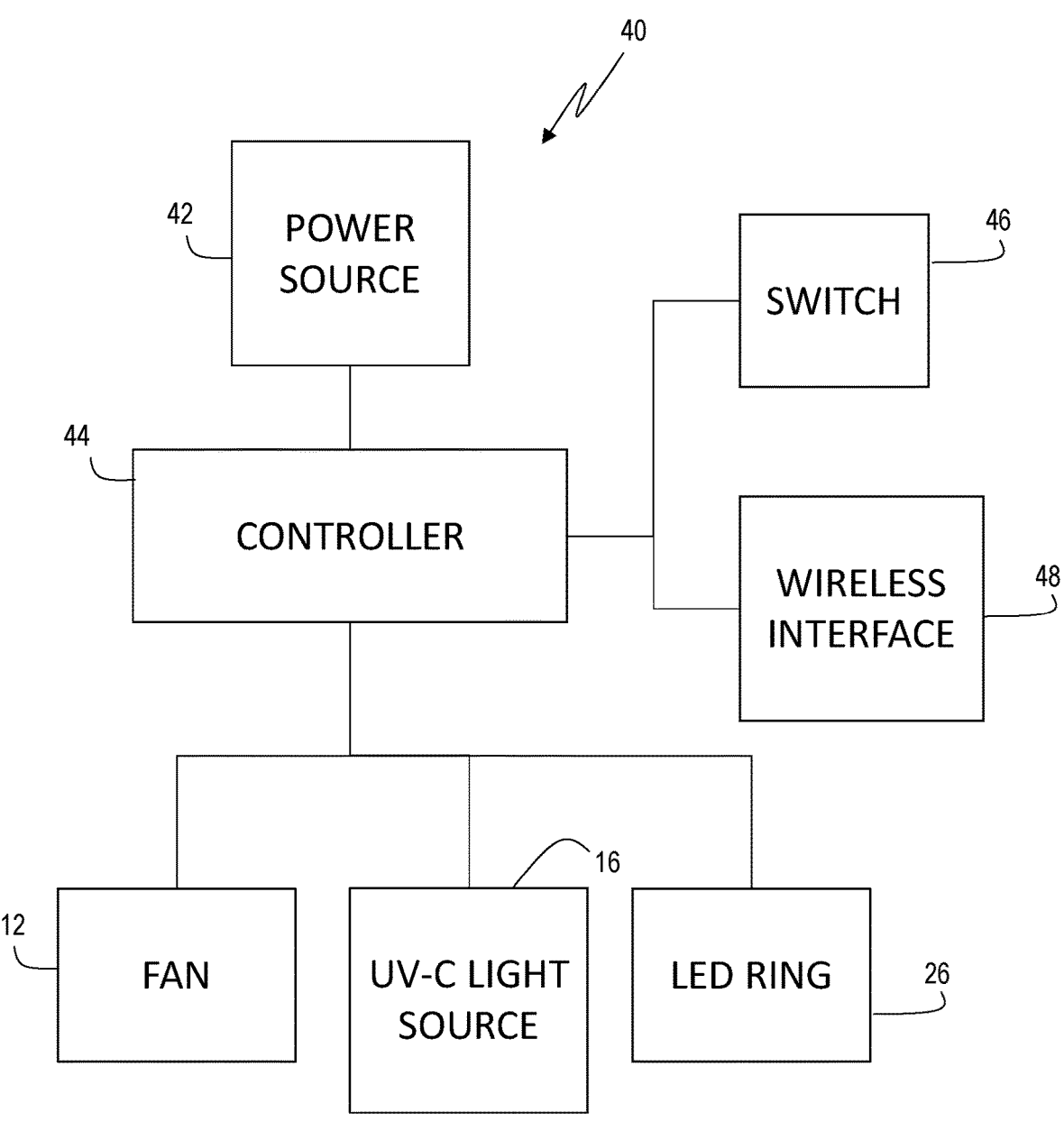
FIG. 3 is a block diagram of a control system for the present invention.

Referring to FIG. 3, torchiere 10 may include control electronics 40 comprising a power source 42 (such as a building power converter) as well as a controller 44 coupled to power source 42 and to fan 12, linear UV-C light source 16, and LED ring 26 for selectively operating each of fan 12, linear UV-C light source 16, and LED ring 26. Controller 44 may thus be programmed to respond to a user input to provide a lighting only mode, an air movement only mode, and a disinfecting mode, or any combination thereof. For example, torchiere 10 may include a user switch 46 for setting the desired mode or a wireless communication interface 48 so that a host device can control torchiere 10 via a wireless connection, such as Wi-Fi or Bluetooth. For many pathogenic particles such as coronavirus virions, the ultraviolet-C fluence required to inactivate 63% of the pathogen particles has been measured. This value is denoted $D_{37}$ and has units of joules per square meter.

In a fan-driven ultraviolet disinfection device, there is a corresponding air flow $S_{37}$ (units of volume per unit time) that will deliver an average ultraviolet fluence of $D_{37}$ during an airborne pathogen's travel through the device. An optimized fan-driven device may use a flow S through the device that will be close to $S_{37}$. Faster flows increase the cost and energy usage but will not substantially increase the rate at which pathogen particles are deactivated. Slower flows lead to lower total rates of pathogen deactivation. The optimal design of a device is thus dependent on the target pathogen and its value of $D_{37}$.

A device optimized for one pathogen may be used for a different one with a different value $D'_{37}$, but will have sub-optimal performance. The present invention includes an electronic control that adjusts the electrical power into the fan in order to match the optimum air flow $S'_{37}$ for the new pathogen. The fan speed can be reduced to accommodate pathogens with larger values of $D_{37}$. This reduction lowers the consumption of electrical power by the device. For pathogens with decreased values of $D_{37}$, the fan speed may be increased to achieve the same rate of deactivating the new pathogen as was achieved with the target pathogen.

What is claimed is:

1. A room air disinfection device, comprising:
a base supporting a reversible fan;
a tube operatively coupled to the reversible fan at a lower end and extending upwardly from the base to an upper end to form a disinfection chamber through which air may flow;
a light block positioned within at least one end of the disinfection chamber and comprising an Archimedes screw; and
an ultraviolet light illumination source extending through at least a portion of the tube.

2. The device of claim 1, further comprising a shade positioned at the upper end of the tube.

3. The device of claim 2, wherein the shade includes a visible light source.

4. The device of claim 3, further comprising a controller programmed to selectively operate the reversible fan, the ultraviolet light illumination source, and the visible light source to provide a mode selected from the group consisting of lighting, air movement, disinfection, and combinations thereof.

5. The device of claim 4, wherein the ultraviolet light illumination source extends linearly along a central axis of the tube.

6. The device of claim 5, wherein the disinfection chamber includes a UVC reflective coating on an inner surface.

7. A method of providing room air disinfection, comprising the steps of:
providing a torchiere having a base supporting a reversible fan, a tube operatively coupled to the reversible fan at a lower end and extending upwardly from the base to an upper end to form a disinfection chamber through which air may flow, a light block positioned within at least one end of the disinfection chamber and comprising an Archimedes screw, and an ultraviolet light illumination source extending through at least a portion of the tube; and
operating the torchiere so that air flows through the disinfection chamber while the ultraviolet light illumination source is powered on.

8. The method of claim 7, wherein the torchiere further comprises a shade positioned at the upper end of the tube.

9. The method of claim 8, wherein the shade includes a visible light source.

10. The method of claim 9, wherein the torchiere further comprises a controller programmed to selectively operate the reversible fan, the ultraviolet light illumination source, and the visible light source to provide a mode selected from the group consisting of lighting, air movement, disinfection, and combinations thereof.

11. The method of claim 10, wherein the ultraviolet light illumination source extends linearly along a central axis of the tube.

12. The method of claim 11, wherein the disinfection chamber includes a UVC reflective coating on an inner surface.

* * * * *